United States Patent [19]

Hori et al.

[11] Patent Number: 4,830,633

[45] Date of Patent: May 16, 1989

[54] DEPILATION METHOD

[75] Inventors: Yutaka Hori; Katsuo Matsumoto; Katsuhiro Yamamoto; Toshimitsu Sasaki; Masayuki Shida, all of Osaka, Japan

[73] Assignee: Nitto Denko Corporation, Osaka, Japan

[21] Appl. No.: 65,094

[22] Filed: Jun. 22, 1987

Related U.S. Application Data

[63] Continuation of Ser. No. 845,225, Mar. 27, 1986, abandoned.

[30] Foreign Application Priority Data

Mar. 27, 1985 [JP]  Japan .................................. 60-64416
May 30, 1985 [JP]  Japan ................................ 60-116896
Feb. 19, 1986 [JP]  Japan .................................. 61-35549

[51] Int. Cl.$^4$ ............................................... C14C 1/06
[52] U.S. Cl. ............................................. 8/160; 8/161
[58] Field of Search ................................... 8/160, 161

[56] References Cited

U.S. PATENT DOCUMENTS 2,067,909  1/1937  Fetter ...................................... 8/160

FOREIGN PATENT DOCUMENTS 518873   11/1955  Canada .
1467756  8/1965   Fed. Rep. of Germany .
2204398  5/1974   France .
52-36111 3/1977   Japan ............................. 252/DIG. 2
798066   7/1958   United Kingdom ......... 252/DIG. 2

OTHER PUBLICATIONS

Chem. Abst. 83:84722m (1975).
Chem. Abst. 94:180497q (1981).
Chem. Abst. 100:91152y (1984).
Hiss et al., *The New Standard Formulary*, pp. 1000–1001 (1910).
Sagarin, *Cosmetics Science & Technology*, pp. 457–478 (1957).

*Primary Examiner*—Frederick E. Waddell
*Attorney, Agent, or Firm*—Sughrue, Mion, Zinn, Macpeak and Seas

[57] ABSTRACT

A depilation method is disclosed, comprising coating a depilatory agent containing an aqueous solution or emulsion of a polymer compound having a film forming ability and a depilatory medicine, drying the resulting coating to form a film and peeling off the film. This method permits to remove hair without causing any pain and producing any unpleasant odor due to the decomposition of hair.

16 Claims, No Drawings

DEPILATION METHOD

This is a Continuation Ser. No. 845,225 filed Mar. 27, 1986 now abandoned.

FIELD OF THE INVENTION

The present invention relates to a depilation method to remove hair without pain.

BACKGROUND OF THE INVENTION

A depilatory agent is practically used in the form of a wax or a cream containing a depilatory medicine.

In the case of a depilatory cream, hair is removed by applying the cream to a position to be depilated, allowing it to stand for a predetermined time, and then wiping off the cream.

In the above method, however, care must be taken in that the cream does not attach to clothes and so on until the effect of the depilatory medicine is exhibited after coating the depilatory cream. In wiping the cream, unpleasant odor due to decomposition of hair by the medicine is generated. Moreover, the skin irritation tends to occur by strongly rubbing.

In the case of wax, hair is removed physically and there is the problem that a strong pain is involved.

SUMMARY OF THE INVENTION

Accordingly, one object of the present invention is to provide a depilation method which can remove hair without pain and generation of unpleasant odor in a short period of time.

Another object of the present invention is to provide a depilation method which can sufficiently remove hair from the root portion thereof by forming a depilatory agent into a film and peeling off the film.

The depilation method according to the present invention comprises coating a depilatory agent containing an aqueous solution or emulsion of a polymer compound having a film forming ability, and a depilatory medicine on a portion where hair is removed, drying the resulting coating to form a film, and then peeling off the film.

DETAILED DESCRIPTION OF THE INVENTION

More specifically, the depilatory method of the present invention includes the following embodiments.

One embodiment is a depilatory method comprising applying a depilatory agent containing an aqueous solution (including a paste and gel) or emulsion of a polymer compound having a film forming ability, a depilatory medicine and, if necessary, a film reinforcing agent onto a depilatory portion, naturally drying the resulting coating to remove the moisture, thereby forming a film, and peeling off the film.

Another embodiment is characterized by a drying means to convert a depilatory agent coated on a depilatory portion into a film. This drying treatment includes a heat treatment using hot air, a treatment utilizing the water absorption capability of a water absorbing sheet, and a heat treatment using hot air after adhering a water absorbing sheet.

Further embodiment is characterized by a peeling manner of a depilatory agent in the form of a film. This includes a method comprising bonding a pressure-sensitive adhesive sheet to the surface of the film of the depilatory agent and peeling off the adhesive sheet together with the film.

The depilatory agent which is used in the present invention contains an aqueous solution or emulsion of a polymer compound having a film forming ability, a depilatory medicine and a film reinforcing agent which is compounded, if necessary. In addition, if necessary, suitable amounts of additives such as an alkali agent, a hair swelling accelerating agent, a filler, a perfume and a coloring agent are compounded.

The depilatory agent using an aqueous polymer compound solution comprises 1 to 70 wt%, preferably 2 to 50 wt%, more preferably 5 to 30 wt%, of at least one water-soluble polymer substance selected from the group of polyvinyl pyrrolidone, polyacrylamide, polyacrylic acid and its salts, polyvinyl alcohol, carboxymethyl cellulose, methyl cellulose, hydroxyethyl cellulose, hydroxypropyl cellulose, gelatin, alginic acid salts, polyethylene glycol, gum arabic, polyvinyl methyl ether and the like, 1 to 15 wt%, preferably 3 to 12 wt%, more preferably 3 to 20 wt%, of at least one depilatory medicine selected from the group of thioglycolic acid or its salts, strontium sulfate, sodium sulfide, potassium sulfide and the like, and the remainder composed of water and the above described other additives, and is designed such that the viscosity is 0.1 to 1,000 poises (at 30° C.), preferably 0.2 to 100 poises (at 30° C.). To adjust the viscosity to such range, a small amount (about 0.1 to 10 wt%) of a viscosity increasing agent can be used. For example, the above described water-soluble high molecular material can be used as the viscosity increasing agent.

The depilatory agent using an emulsion of a polymer compound comprises 1 to 70 wt%, preferably 20 to 60 wt%, more preferably 30 to 55 wt%, of at least one water-insoluble polymer substance selected from the group of rubbers such as natural rubber and synthetic rubber, polyvinyl acetate, ethylenic copolymers, wax, homo- or copolymers of (meth)acrylic esters such as methyl (meth)acrylate, ethyl (meth)acrylate, butyl (meth)acrylate, 2-ethylhexyl (meth)acrylate, isooctyl (meth)acrylate and decyl (meth)acrylate, and copolymers of polar monomers having a functional group such as an amino group, and amido group, a hydroxyl group, a carboxyl group and an epoxy group, or polar monomers not having a functional group such as (meth)acrylonitrile, vinyl acetate, styrene, vinyl pyrrolidone and vinyl ether, and the above descried (meth)acrylic acid esters, 1 to 15 wt%, preferably 3 to 12 wt%, more preferably 3 to 10 wt%, of the above described depilatory medicine, and the remainder composed of water and the above described other additives, and is designed such that the viscosity is 0.1 to 1,000 poises (at 30° C.) and preferably 0.2 to 100 poises (at 30° C.).

Examples of the alkali agents are the ammonium salt or metal salt of organic dicarboxylic acid, potassium hydroxide, calcium hydroxide, and sodium hydroxide. The alkali agent can be compounded in an amount of 0.1 to 5 wt%, preferably 0.5 to 3 wt%, based on the weight of the depilatory agent.

Examples of the film reinforcing agent are natural, synthetic or inorganic short fibers having a length of 0.1 to 14 mm, preferably 1 to 10 mm and a diameter of 1 to 50 μm, preferably 1 to 10 μm. The amount of the film reinforcing agent compounded is 1 to 30 wt% and preferably 2 to 15 wt% based on the weight of the depilatory agent. For the purpose of increasing the film reinforcing effect, 1 to 35 wt% of silicon dioxide, calcium carbonate, clay, kaolin, aluminum hydroxide or the like can be used. These compounds also act as fillers.

An example of the hair swelling accelerating agent is urea. Furthermore, for the purpose of increasing the flexibility of the film, in the case of a water-soluble depilatory agent, polyvalent alcohols such as glycerin can be used in an amount of 1 to 15 wt% based on the weight of the depilatory agent, and in the case of an emulsion type depilatory agent, a plasticizer comprising phthalic acid derivatives such as dioctyl phthalate and dibutyl phthalate can be used in an amount of 1 to 15 wt% based on the weight of the depilatory agent.

The thus compounded depilatory agent is coated usually in an amount (thickness) of 0.01 to 3 mm, preferably 0.1 to 1 mm, although the amount of the depilatory agent varies depending on the applied portion such as a hand and a leg.

A predetermined amount of the depilatory agent is coated, and under conditions that the moisture is dissipated at a high temperature, for example, in the summer season, the resulting coating is allowed to dry in the natural atmosphere to thereby form a film. Upon peeling off the film, hair the root of which has been weakened by the depilatory medicine can be sufficiently removed, not leaving any film at the depilatory portion.

In peeling off the film of the depilatory agent, when the depilatory agent is the emulsion type, the film becomes transparent with decreasing water due to evaporation of moisture and, therefore, the dry condition can be relatively easily determined visually and the depilation operation can be carried out without an error.

Film formation of the depilatory agent coated on a portion to be depilated can be accelerated by, as well as the above natural drying method, an additional drying means. It can be understood from the explanation as described hereinafter that the additional drying means facilitates the depilation operation in addition to the film formation.

One of such drying means is a heat treatment with hot air. This heat treatment is preferably conducted after allowing to stand the depilatory agent for several minutes after coating, thereby impregnating the depilatory medicine in the depilatory agent in the hair. Usually the drying is carried out at 50° to 200° C. for 1 to 10 minutes. The heat source is sufficient to be a home drier.

The film thus formed can be peeled off as such to achieve the depilation. If, in this case, a pressure-sensitive adhesive sheet is bonded to the surface of the film and peeled off together with the film, the film can be peeled off without leaving any pieces because the film and the pressure-sensitive sheet are strongly bonded.

Suitable pressure-sensitive adhesive sheet is a pressure-sensitive adhesive sheet which is prepared by coating a film-like substrate having flexibility and pliability, such as a plastic film, paper, nonwoven fabric and cloth, each having a thickness of about 5 to 100 μm, with an adhesive substance made mainly of rubber and/or synthetic resin and having pressure-sensitive adhesiveness at ordinary temperature (30° C.) in a thickness of about 5 to 200 μm. More preferred sheet is a sheet which has an adhesive force to a bakelite plate of about 20 to 2,000 g/cm (180° peeling adhesive force at 25° C., tensile speed: 300 mm/min). The size of the sheet is not critical, and the sheet may be equal to or larger or smaller than the film of the dipilatory agent. If the sheet has a larger area than the film, the depilation operation is simplified because a portion extending from the edge of the film forms a part for the separation. When the sheet has a smaller surface area than the film, it is convenient to form a pick up portion of the film by peeling off a part of the film.

Another drying means is as follows. A water absorption sheet is bonded to the depilatory agent coated and, if necessary, heat treatment is applied from the side of the water absorption sheet bonded.

In accordance with this drying means, the water absorption sheet absorbs the water contained in the depilatory agent coated in a short period of time to form a film, the film is peeled off together with the sheet to achieve the depilation or only the sheet is peeled off from the film and then the above pressure-sensitive adhesive sheet is bonded to the film and the film is peeled off together with the sheet to remove hair. In this way, the film can be removed without leaving any piece on a portion to be depilated. When, in this case, heating is applied in combination, the drying time for forming the coating can be shortened.

As the water absorption sheet, any sheet-shaped material can be used so long as it is capable of absorbing water. For example, when a porous sheet material (preferably having a thickness of 5 to 100 μm) such as hydrophilic nonwoven fabrics, paper, cloth and foamed sheets is used, the sheet material is integrally combined by placing it on the depilatory agent coated which is still in a wet condition and then slightly pressing, and by drying the assembly in that state, the film is peeled off together with the water absorption sheet to remove the hair.

Preferred examples of other water absorption sheets are as follows. A film or sheet of a high water absorption polymer having a water absorption ratio of 10 to 1,000 times (by weight) the weight thereof which is prepared by introducing suitable intramolecular cross-linking into a water-soluble polymer having a hydrophilic group such as a hydroxyl group, a carboxyl group or its salt, and which is insoluble in water, such as a polymer prepared by graft polymerization of (meth)acrylic acid, (meth)acrylonitrile, and maleic anhydride onto starch, cross-linked product of a copolymer of α-olefin having 2 to 12 carbon atoms and maleic anhydride or its derivative, or alkali neutralized product, and polyacrylic acid salt; and nonwoven fabrics, paper and foamed products and so forth in the inside or on the surface of which the above high water absorption polymer is dispersed or laminated. The water absorption sheet made of such a high water absorption polymer absorbs water in the depilatory agent due to the water absorption capability and a coating having the desired physical strength can be formed.

The water content of the depilatory agent formed into a film by the drying treatment is controlled so as to be 0.1 to 10 wt% when the heating treatment is applied in combination, or to be 10 to 40 wt% when the heating treatment is not applied, so that the physical pain at the time of depilation can be reduced and the depilatory effect can be exhibited.

The depilation method of the present invention has the following advantages. Unpleasant odor is not generated because the odor due to decomposition of hair by a depilatory medicine is masked with a polymer compound having a film forming ability. Serious pain is not felt by the medical action of the depilatory medicine. Hair can be removed without leaving any residue by using a pressure-sensitive sheet or a water absorption sheet in combination.

The present invention is described in greater detail by reference to the following examples. Unless otherwise indicated, all percents, parts, ratios and the like are by weight.

EXAMPLE 1

| | |
|---|---|
| Polyacrylamide | 15% |
| Calcium Thioglycolate | 7% |
| Silicon Dioxide | 3% |
| Calcium Hydroxide | 2% |
| Glycerin | 5% |
| Water | 68% |

A composition consisting of the above components was dissolved in water to prepare a uniform aqueous polymer compound solution (100 poises at 30° C.). This depilatory agent was coated 50 to 300 μm and allowed to stand for about 5 minutes and the portion was heated with a drier. In 5 minutes, a film (water content: 4 to 5 wt%) was formed and hair was in the condition that it was trapped in the film. Since the strength of hair was reduced or the hair was dissolved by the effect of the depilatory medicine, pain was not caused when the film was peeled off from the skin and residue was not left on the portion.

EXAMPLE 2

| | |
|---|---|
| Natural Rubber Latex (50% base) | 91% |
| Sodium Thioglycolate | 7% |
| Sodium Hydroxide | 2% |
| | 100% |

A composition consisting of the above components and a small amount of polyvinyl pyrrolidone as a viscosity increasing agent was mixed to prepare a uniform emulsion (30 poises at 30° C.). This depilatory agent was coated on a portion to be depilated in a thickness of about 200 to 400 μm in the same manner as in Example 1 and allowed to stand for about 5 minutes, and the portion was heated with a drier. A film (water content: 1 to 3 wt%) which was substantially transparent was formed, and by peeling off the film, the hair was removed without any pain.

EXAMPLE 3

The depilatory agent of Example 1 was uniformly coated on a portion to be depilated in a size of about 5×10 cm in a thickness of about 300 μm and allowed to stand for about 5 minutes, and the portion was then heated with a drier. In 5 minutes, a film was formed, and hair was trapped in the film. A pressure-sensitive adhesive sheet piece having a width of 5 cm and a length of 11 cm (adhesive force to a bakelite sheet: 100 g/cm), with a polyisobutylene pressure-sensitive adhesive layer (thickness: 50 μm) provided on the surface thereof was bonded to the above film. The sheet was peeled off together with the film by picking up the edge of the sheet not bonded to the film to remove the hair. Since the strength of the hair was reduced or the hair was dissolved by the effect of the depilatory medicine, the film could be removed together with the sheet without any pain, and furthermore the hair was completely removed without leaving any film residue on the portion.

EXAMPLE 4

| | |
|---|---|
| Methyl Methacrylate-Acrylic Acid/2-Ethylhexyl Copolymer Emulsion (solids content: 40% base) | 90% |
| Calcium Thioglycolate | 7% |
| Calcium Hydroxide | 3% |
| | 100% |

A composition consisting of the above components and a small amount of polyvinyl pyrrolidone was mixed to prepare a uniform emulsion (30 poises at 30° C.). This depilatory agent was coated on a portion to be depilated in a size of about 5×10 cm in a thickness of about 200 μm in the same manner as in Example 3 and allowed to stand for about 5 minutes, and the portion was heated with a drier to form a nearly transparent film (water content: 1 to 2 wt%). After making the film transparent, the same pressure-sensitive adhesive sheet as used in Example 3 was bonded. When peeling off the sheet together with the shet, hair was completely removed without any pain, and furthermore a film residue was not left.

EXAMPLE 5

The same depilatory agent as used in Example 1 was coated on a portion to be depilated in a size of about 5×20 cm in a thickness of about 100 to 300 μm, and a rayon nonwoven fabric having a width of 6 cm and a length of 12 cm was bonded thereto, followed by allowing to stand for about 5 minutes, and the portion was heated with a drier. In 5 minutes, a film was formed, and the hair was trapped in the film. This film was peeled off together with the nonwoven fabric by pulling the edge of the nonwoven fabric remaining unbonded to the film. Since the strength of the hair was reduced or the hair was dissolved by the effect of the depilatory medicine, the film could be removed together with the nonwoven fabric without any pain, and the hair could be removed without leaving any residue on the portion.

EXAMPLE 6

| | |
|---|---|
| Styrene/2-Ethylhexyl Acrylate Copolymer Emulsion (solids content: 40% base) | 90% |
| Calcium Thioglycolate | 7% |
| Calcium Hydroxide | 3% |
| | 100% |

A composition consisting of the above components and a small amount of polyvinyl pyrrolidone was mixed to prepare a uniform emulsion (30 poises at 30° C.). This depilatory agent was coated on a portion to be depilated in a size of about 5×10 cm in a thickness of about 300 to 500 μm in the same manner as in Example 5, and a cotton cloth having a width of 6 cm and a length of 12 cm was then bonded thereto. The portion was heated for about 4 minutes with a drier to form a film (water content: 3 to 4 wt%). When peeling off the film together with the cotton cloth, the hair could be removed completely without any pain, and furthermore any film residue was not left.

EXAMPLE 7

| | |
|---|---|
| Sodium Thioglycolate | 10% |
| Polyvinyl Acetate Emulsion | 88% |

| | |
|---|---|
| (solids cotent: 50%) | |
| Caustic Soda | 2% |

A composition consisting of the above components was dissolved in water to prepare an aqueous dispersion of depilatory agent (20 poises at 30° C.).

This depilatory agent was coated on an underarm hair of each of 10 paneller (female adults) in an amount of about 700 g/m². A water absorbing paper was adhered to the surface of the film and was allowed to stand for about 15 minutes. The water absorbing paper was peeled off and the film (water content: about 10 wt%) was then peeled off to remove the hair.

Any unpleasant odor due to the decomposition of the hair by the depilatory treatment was not substantially generated, and visual observation confirmed that skin irritation was not substantially produced.

EXAMPLE 8

A film was prepared in the same manner as in Example 7 except that the amount of the depilatory agent was reduced to about 200 g/m². To this film was bonded a pressure-sensitive adhesive sheet comprising a 30 μm thick polyethylene film and the same pressure-sensitive adhesive layer as in Example 3 provided on the polyethylene film to conduct the depilation treatment. The same good results as in Example 1 were obtained.

EXAMPLE 9

A water-soluble depilatory agent (80 poises at 30° C.) consisting of 7% sodium thioglycolate, 1% of caustic soda and 77% of purified water was prepared.

This depilatory agent was coated on an underarm portion of each of 10 panellers in an amount of about 500 g/m². A high water absorption polymer comprising a polyurethane foam (thickness: 0.8 mm) with a polyacrylic acid salt dispersed therein was bonded to the coated surface and was allowed to stand for about 10 minutes. The assembly was peeled off to remove the hair. The film contained about 30 wt% of water and the depilation effect was good as in Example 1.

EXAMPLE 10

A water-soluble depilatory agent (100 poises at 30° C.) consisting of 5% calcium thioglycolate, 20% polyvinyl pyrrolidone, 2% calcium hydroxide, 1% silicon dioxide and 72% of distilled water was prepared.

This depilatory agent was coated on an underarm hair of each of 10 panellers in an amount of about 500 g/m². A nonwoven fabric with a high water absorption polymer layer made of a starch/acrylic acid graft copolymer and having a thickness of 1,000 μm formed on the surface thereof was bonded through a polymer layer and was allowed to stand for about 8 minutes. The assembly was peeled off to remove the hair. The film contained about 30 wt% of water, and the depilatory effect was good as in Example 1.

EXAMPLE 7

| | |
|---|---|
| Methyl Methacrylate/2-Ethylhexyl Acrylate Copolymer Emulsion (solids content: 38% base) | 86% |
| Calcium Thioglycolate | 7% |
| Vinylon Short Fibers (length: 3 mm, diameter: 2 to 4 μm) | 5% |
| Calcium Hydroxide | 2% |
| | 100% |

A composition consisting of the above components and a small amount of polyvinyl pyrrolidone was mixed with water to form a uniform polymer compound-containing emulsion (35 poises at 30° C.). This depilatory agent was coated on a portion to be depilated in a thickness of about 100 to 300 μm and allowed to stand for about 5 minutes, and the portion was treated by heating with a drier. In 5 minutes, a film was formed, and the hair was trapped in the film. Since the hair was reduced in strength or dissolved by the effect of the depilatory medicine, the film could be removed without any pain. Furthermore, the hair could be completely removed without leaving any residue.

While the invention has been described in detail and with reference to specific embodiments thereof, it will be apparent to one skilled in the art that various changes and modifications can be made therein without departing from the spirit and scope thereof.

What is claimed is:

1. A depilation method which comprises coating a depilatory agent containing an aqueous solution or emulsion of a polymer compound having a film forming ability and present in an amount effective to form a film, and as a depilatory, thioglycolic acid or a salt thereof, strontium sulfate, sodium sulfide or potassium sulfide in an amount effective to act as a depilatory, on a portion of skin where hair is to be removed, drying the resulting coating by bonding a water absorption sheet to the depilatory agent coated to form a film and peeling off the film.

2. The method as in claim 1, wherein the polymer compound having a film forming ability is a water-soluble or water-insoluble polymer substance.

3. The method as in claim 2, wherein the water-soluble polymer substance is at least one selected from the group consisting of polyvinyl pyrrolidone, polyacrylamide, polyacrylic acid and its salts, polyvinyl alcohol, carboxymethyl cellulose, hydroxypropyl cellulose, gelatin, alginic acid salts, polyethylene glycol, polyvinyl methyl ether and gum arabic.

4. The method as claimed in claim 2, wherein the water-insoluble polymer substance is at least one selected from the group of natural rubber, synthetic rubber, polyvinyl acetate, homo- and copolymers of acrylic acid or methacrylic acid esters, and copolymers of polar monomers containing or not containing a functional group selected from the grup consisting of amino, amido, hydroxyl, carboxyl and epoxy.

5. The method as in claim 1, wherein the viscosity of the depilatory agent is 0.1 to 1,000 poises at 30° C.

6. The method as in claim 2, wherein the depilatory agent comprises 1 to 15 wt% of said thioglycolic acid or salt thereof, strontium sulfate, sodium sulfide or potassium sulfide, 1 to 70 wt% of a water-soluble polymer substance and water, said agent being in the form of an aqueous solution.

7. The method as in claim 2, wherein the depilatory agent comprises 1 to 15 wt% of said thioglycolic acid or salt thereof, strontium sulfate, sodium sulfide or potassium sulfide, 1 to 70 wt% of a water-insoluble polymer substance and water, said agent being in the form of an emulsion.

8. The method as in claim 6, wherein the depilatory agent further contains 0.1 to 5 wt% of an alkali agent.

9. The method as in claim 7, wherein the depilatory agent further contains 0.1 to 5 wt% of alkali agent.

10. The method as in claim 1, wherein the drying treatment is conducted utilizing in combination the water absorbing capability of the water absorbing sheet and a heating treatment.

11. The method as in claim 10, wherein the heating treatment is conducted at 50° to 200° C. for 1 to 10 minutes.

12. The method as in claim 1, wherein the water content of the film is 0.1 to 40 wt%.

13. The method as in claim 1, wherein a pressure-sensitive adhesive sheet is adhered to the surface of the film and the assembly is peeled off.

14. The method as in claim 13, wherein the size of the pressure-sensitive adhesive sheet is larger than the film.

15. The method as in claim 1, wherein the depilatory agent further contains a film-reinforcing agent.

16. The method as in claim 15, wherein the film-reinforcing agent is a short fiber.

* * * * *